(12) United States Patent
Larsson (10) Patent No.: US 11,510,560 B2
(45) Date of Patent: Nov. 29, 2022

(54) ARRANGEMENT FOR CLEANING AND DISINFECTION OF ENDOSCOPES

(71) Applicant: Luki AB, Stockholm (SE)

(72) Inventor: Michael Larsson, Stockholm (SE)

(73) Assignee: LUKI AB, Stockholm (SE)

( * ) Notice: Subject to any disclaimer, the term of this patent is extended or adjusted under 35 U.S.C. 154(b) by 91 days.

(21) Appl. No.: 16/647,489

(22) PCT Filed: Sep. 15, 2017

(86) PCT No.: PCT/SE2017/050911
§ 371 (c)(1),
(2) Date: Mar. 14, 2020

(87) PCT Pub. No.: WO2019/054910
PCT Pub. Date: Mar. 21, 2019

(65) Prior Publication Data
US 2020/0214548 A1    Jul. 9, 2020

(51) Int. Cl.
| | | |
|---|---|---|
| *A61B 1/12* | (2006.01) | |
| *A61B 1/00* | (2006.01) | |
| *A61L 2/18* | (2006.01) | |
| *A61L 2/24* | (2006.01) | |
| *B08B 9/032* | (2006.01) | |
| *B08B 9/043* | (2006.01) | |

(52) U.S. Cl.
CPC .......... *A61B 1/123* (2013.01); *A61B 1/00059* (2013.01); *A61B 1/122* (2013.01);
(Continued)

(58) Field of Classification Search
CPC ......... A61B 1/123; A61B 1/122; A61B 1/125; A61B 1/00059; A61B 50/34; A61L 2/18;
(Continued)

(56) References Cited

U.S. PATENT DOCUMENTS

| | | |
|---|---|---|
| 2001/0041825 A1 | 11/2001 | Shibata et al. |
| 2005/0065405 A1 | 3/2005 | Hasegawa |
| 2007/0234495 A1 | 10/2007 | Suzuki et al. |

(Continued)

FOREIGN PATENT DOCUMENTS

| | | |
|---|---|---|
| CN | 205554719 U | * 9/2016 |
| DE | 102013202540 A1 | 8/2014 |

(Continued)

OTHER PUBLICATIONS

Machine translation: CN205554719; Xu, J. (Year: 2016).*
International Search Report from corresponding International Application PCT/SE2017/050911 dated Jun. 11, 2018, 6 pages.

*Primary Examiner* — Natasha N Campbell
(74) *Attorney, Agent, or Firm* — Cooper Legal Group, LLC; Ronald M. Kachmarik (57) ABSTRACT

An arrangement, and associated method, for cleaning and disinfecting an endoscope having an internal channel accessible via an opening. The arrangement includes: a support structure; at least one tray including at least one fixture arranged to maintain the endoscope in the desired position within the tray; a rack arranged to support the tray; a control unit arranged to control and operate the arrangement; a user interface connected to the control unit and arranged to make it possible for an operator to indicate the type of endoscope arranged in the tray; an optical device connected to the control unit and configured to confirm the type of endoscope arranged in the tray; a robotic device operated by the control unit and arranged to clean the at least one channel in the endoscope arranged in the tray; and a disinfector device arranged to enclose the tray and disinfect the endoscope.

21 Claims, 5 Drawing Sheets

(52) U.S. Cl.
CPC ............... *A61B 1/125* (2013.01); *A61L 2/18* (2013.01); *A61L 2/24* (2013.01); *B08B 9/0325* (2013.01); *B08B 9/0436* (2013.01); *A61L 2202/122* (2013.01); *A61L 2202/14* (2013.01); *A61L 2202/17* (2013.01); *A61L 2202/24* (2013.01); *B08B 2209/04* (2013.01)

(58) Field of Classification Search
CPC .. A61L 2/24; A61L 2202/122; A61L 2202/14; A61L 2202/17; A61L 2202/24; B08B 9/0325

See application file for complete search history.

(56) References Cited

U.S. PATENT DOCUMENTS

| | | |
|---|---|---|
| 2009/0044845 A1 | 2/2009 | Cui et al. |
| 2009/0103836 A1 | 4/2009 | Shimizu et al. |
| 2009/0119856 A1 | 5/2009 | Onishi |
| 2011/0005342 A1* | 1/2011 | Treat ..................... A61L 2/22 73/865.8 |
| 2011/0097248 A1 | 4/2011 | Tomita et al. |
| 2011/0262250 A1 | 10/2011 | Treat et al. |
| 2014/0170020 A1* | 6/2014 | Hiruta ..................... A61L 2/16 422/28 |
| 2017/0172398 A1 | 6/2017 | Carlson |
| 2017/0252473 A1 | 9/2017 | Thompson et al. |

FOREIGN PATENT DOCUMENTS

| | | |
|---|---|---|
| WO | 2017060390 A1 | 4/2017 |
| WO | 2017077073 A1 | 5/2017 |

\* cited by examiner

ARRANGEMENT FOR CLEANING AND DISINFECTION OF ENDOSCOPES

TECHNICAL FIELD

The present invention relates to an arrangement for cleaning and disinfection of endoscopes or other surgical instruments, and a corresponding method for cleaning and disinfection of an endoscope or other surgical instruments.

BACKGROUND

During medical examination or treatment different surgical instruments and models of endoscopes are frequently used to take tissue samples, treat different areas within the human body and/or make it possible to visually inspect different areas with the human body.

Endoscopes, and other surgical instruments, are complex and expensive and therefor cleaned and disinfected after use such that each endoscope or other surgical instruments could be used a number of times.

However, the cleaning process of the complex endoscopes is complicated and requires that the interior, the channels and openings of the endoscopes are cleaned manually before the endoscope is disinfected. The manual cleaning involves manual handling of the contaminated used endoscopes and unfortunately expose the person involved for a potential risk of exposure to contaminants. Furthermore, the manual cleaning and handling of the complex endoscopes involves a risk that the cleaning is not performed correctly to ensure that the desired result after cleaning and disinfection is achieved.

It is therefore a need for an improved arrangement for cleaning and disinfection of endoscopes as well as an improved method for conducting the cleaning and disinfection to reduce the described problems.

SUMMARY OF THE INVENTION

The present invention relates to an arrangement for cleaning and disinfection of endoscopes, and a corresponding method for cleaning and disinfection of an endoscope that to at least some extent eliminates, or reduces, the drawbacks mentioned above. Preferable embodiments of the arrangement and the method are defined in the dependent claims, The arrangement according to the invention is intended for cleaning and disinfection of endoscopes comprising at least one internal channel accessible via an opening in the endoscope, and said arrangement comprises:
  a support structure;
  at least one tray comprising at least one fixture arranged to maintain the endoscope in the desired position within the tray;
  a rack arranged to support the tray;
  a control unit arranged to control and operate the arrangement;
  a user interface connected to the control unit and arranged to make it possible for an operator to indicate the type of endoscope arranged in the tray;
  an optical device connected to the control unit and configured to confirm the type of endoscope arranged in the tray;
  a robotic device operated by the control unit and arranged to clean the at least one channel in the endoscope; and
a disinfector device arranged to enclose the tray and disinfect the endoscope.

The arrangement according to the invention has several advantages compared to prior art solutions for cleaning and disinfection of endoscopes. First, the arrangement ensures that each type of endoscope is correctly cleaned since the operator first indicates the type of endoscope packed in the tray via the user interface and the optical device verify the type of endoscope is packed in the tray before the cleaning is initiated. If the manual indication and the verification differs the control unit is configured to alert the user that something is wrong. Secondly, the manual handling of the endoscope is reduced considerably since the cleaning process is performed automatically without any involvement of the operator which reduces the exposure to potentially contaminations. Third, the arrangement reduces the time for cleaning and disinfecting endoscopes, and consequently also the cost for the cleaning and disinfection process. Furthermore, the arrangement reduces the risk for damages to the endoscope caused by improper handling of the endoscope by the operator considerably and ensures a uniform cleaning and disinfection result for every endoscope that is cleaned and disinfected by the arrangement.

According to one embodiment of the arrangement, the at least one tray comprises a fixture arranged to maintain the endoscope in a position where it is accessible for the robotic device, and at least one adapter intended to be connected to the at least one channel in the endoscope. The fixture ensures that the endoscope is easy for the robotic device to grip and perform the cleaning of the at least one channel in the endoscope. The robotic device is furthermore configured to, after the cleaning is completed, connect the at least one channel of the endoscope with the adapter to make it possible to flush disinfection fluid through the at least one channel when the tray is arranged in the disinfector device.

According to one embodiment of the arrangement, the fixture is removably arranged in the tray. This embodiment is favorable since the operator can select a fixture suitable for the type of endoscope that needs to be cleaned.

According to one embodiment of the arrangement,the arrangement furthermore comprises a working fixture arranged separated from the tray, said working fixture comprises means for maintain the endoscope in a secured position where it is accessible for the robotic device to facilitate for the robotic device to access the at least one channel in the endoscope.

According to one embodiment of the arrangement, the optical device furthermore is configured to monitor that the endoscope is arranged in the intended position in the tray and that the at least one adapter is connected to the at least one channel in the endoscope to further ensure that the desired final disinfection result is achieved.

According to one embodiment of the arrangement, the robotic device is configured to dismount one or more parts of the endoscope to access the at least one channel in the endoscope. This embodiment is favorable since this embodiment of the arrangement could be used for cleaning more complex type of endoscopes.

According to one embodiment of the arrangement, the robotic device comprises means for brushing the at least one channel with an appropriate brush, and i or comprises means for flushing the at least one channel in the endoscope with an appropriate cleaning fluid or an abrasive cleaning material.

According to one embodiment of the arrangement, the arrangement further comprises a casing arranged to enclose the robotic device. This embodiment is very favorable since the robotic device is enclosed by the casing thereby reducing the risk for the operator to be exposed to contaminants considerably during the cleaning process and handling of the endoscope.

According to one embodiment of the arrangement, the rack is arranged within the casing and a closable opening is arranged in the casing to access the rack. This embodiment is favorable since the operator only need to arrange the endoscope in the tray, and enter the tray in the rack via the opening in the casing. Once the opening is closed and sealed, the cleaning of the endoscope could be started within the enclosed space inside the casing.

According to one embodiment of the arrangement, the casing extend to the disinfection device such that the cleaning of the endoscope takes place within the casing. This embodiment of the casing minimizes the risk for exposure between the endoscope, the robotic device and the user.

According to one embodiment of the arrangement, the disinfector device is arranged to flush one or more disinfection fluids on the endoscope and through the at least one channel according to a predetermined procedure to disinfect the endoscope.

According to one embodiment of the arrangement, the disinfector device is arranged to involve two different disinfection fluids during the disinfection process. The use of two different types of fluid improves the result of the disinfection since the different fluids could be adapted to different types of contaminations.

According to one embodiment of the arrangement, the disinfector device is arranged to conduct a number of predetermined steps to disinfect the endoscope.

According to one embodiment of the arrangement, the disinfector device comprises a disinfection chamber arranged to enclose the tray, and said disinfection device is configured to operate according to a predetermined program to distribute a disinfection fluid within the disinfection chamber to disinfect the endoscope.

According to one embodiment of the arrangement, the disinfection device is arranged within the casing and comprises a disinfection sink such that the tray is arranged in the sink where the disinfection process takes place.

According to one embodiment of the arrangement, the arrangement further comprises means to generate a pressure inside the casing below that of the atmosphere surrounding the casing to maintain contaminations within the casing.

The invention furthermore relates to a method for cleaning and disinfection of an endoscope comprising at least one internal channel accessible via an opening in the endoscope using the arrangement defined above. The method comprising the steps:
  a) arrange the endoscope in the intended position in the tray;
  b) indicate the type of endoscope via the user interface;
  c) verifying the type of endoscope with the optical device;
  d) activate the robotic device to dean the at least one channel in the endoscope;
  e) activate the disinfector device to disinfect the endoscope;

The method according to the invention ensures a uniform cleaning and disinfection process for all endoscopes. Furthermore, each type of endoscope will be correctly cleaned since both the operator and the optical device verify the present type of endoscope before the cleaning is initiated.

In one embodiment of the method, the arrangement furthermore comprises a working fixture arranged separated from the tray, said working fixture comprises means for maintain the endoscope in a secured position where it is accessible for the robotic device, and said method comprises an additional step c2) conducted after step c) and before step d) in which the robotic device moves the endoscope and secures it in the working fixture.

One embodiment of the method, used in combination with an arrangement comprising a tray with at least one adapter intended to be connected to the at least one channel in the endoscope, comprises an additional step conducted after step d and involves connecting the at least one adapter to the at least one channel in the endoscope to be able to flush disinfection fluid through the at least one channel in the endoscope.

In one embodiment of the method, the method comprises an additional step conducted after step d where the optical device monitors that the endoscope is arranged in the intended position in the tray and that the at east one adapter is connected to the at least one channel in the endoscope.

In one embodiment of the method, the robotic device initiates step d) by dismounting one or more parts of the endoscope to access the at least one channel in the endoscope. This embodiment is favorable if the endoscope has a complex design which requires that one or more parts are dismounted to access the at least one channel in the endoscope to ensure that all components and the at least one channel are cleaned and disinfected.

In one embodiment of the method, step d) is performed in combination with a robotic device comprising means for brushing the at least one channel with an appropriate brush, and/or comprises means for flushing the at least one channel in the endoscope with an appropriate cleaning fluid or an abrasive cleaning material.

In one embodiment of the method, the disinfector device during step f) is arranged to conduct a number of predetermined steps to disinfect the endoscope to ensure the desired disinfection of the at least one channel in the endoscope, the endoscope as well as parts removed from the endoscope.

One embodiment of the method furthermore comprises a cleaning step conducted after step d), wherein said robotic device during this step is configured to clean the space within the casing to remove residues from the cleaning process.

In one embodiment of the method, the disinfector device comprises a disinfection chamber arranged to enclose the tray, and said disinfection device during step f) is configured to operate according to a predetermined program to distribute a disinfection fluid within the disinfection chamber to disinfect the endoscope.

Further scopes of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular parts of the arrangement described. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The arrangement according to the present invention is schematically illustrated in the appended figures.

DETAILED DESCRIPTION

The arrangement 20 according to the invention will now be described in detail with reference to the appended figures.

There are a number of different types of endoscopes adapted for different purposes, as well as different sizes for adults and children. The endoscopes are used for taking tissue samples, treatment of different areas within the human body and/or make it possible to visually inspect different areas with the human body.

Figure 1:
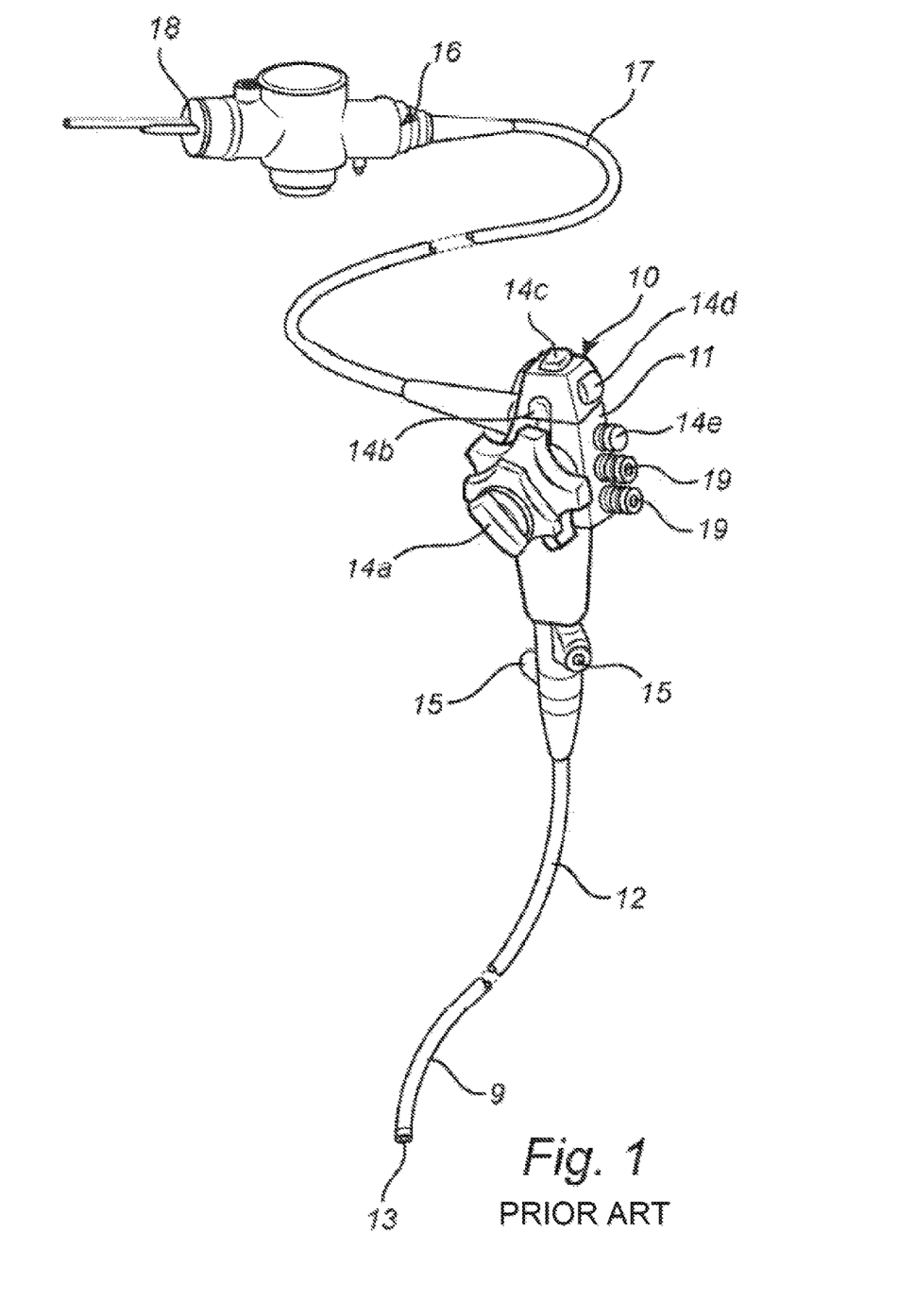
FIG. 1 illustrates a perspective view of one embodiment of an endoscope.

One example of an endoscopes 10 is illustrated in perspective in FIG. 1. The endoscope comprises an endoscope control body 11 and an elongated insert tube 12 extending from the endoscope control body. The end of the insert tube opposite the endoscope control body is referred to as the bending section 9 that is movable and operated from the endoscope control body. The bending section is ended by a tip head 13 in which for example a camera head and lighting means could be arranged.

The endoscope control body comprises control means 14a, 14b, 14c, 14d, 14e arranged to operate and control the bending section 9 of the insert tube 12, and the different functions of the endoscope. One of the control means 14a is configured to operate the movement of the bending section of the insertion tube 12 while the other control means could be configured to for example switch on or off the light, activate a flow of water and air, and start the suction of fluid from the area of the tip head 13.

In the endoscope control body instrument openings 15 are formed to make it possible to access corresponding instrument channels extending within the insert tube. The instrument channels could be used to guide means for taking tissue samples or instruments for treatment of an area within the human body.

The illustrated endoscope 10 furthermore comprises a connector body 16 arranged in the end of a universal cord 17 extending from the connector body to the endoscope control body. The connector body 16 furthermore comprise a connector 18 intended for connecting the endoscope 10 to a corresponding coupling element arranged on a not illustrated endoscope control and support unit arranged to support the endoscope with for example power, light, suction, air and/or water fed to the endoscope via channels in the universal cord 17. The universal cord 17 comprises a number of channels arranged to deliver for example electrical power, water, suction, air or inert gas to the bending section tip head of the endoscope. The universal cord 17 could furthermore comprise a fiber element, or a wire, to transfer optical information from bending section tip head to the endoscope control unit where the information is stored and processed to be presented for an operator or doctor.

All channels within the endoscope insertion tube and the universal cord must be cleaned and disinfected after being used to prevent contaminants from being transferred from one patient to another. In the endoscope control body, the two instrument openings 15 and two openings 19, formed in the endoscope control body, makes it possible to access corresponding channels that extend in the insertion tube and the universal cord of the endoscope to clean the respective channel.

The two openings in the endoscope control body are sealed by a channel closing adapter during use of the endoscope. The channel closing adapter is during the cleaning process dismounted and replaced by a brush guide adapter that is fitted in the opening to facilitate the insertion of the brush and guide the brush in the right direction within the insertion tube and the universal cord to ensure that the respective channel is cleaned in both directions starting from the endoscope control body.

The instrument openings could also comprise an instrument adapter that needs to be dismounted before cleaning to access the instrument channel. However, this channel only extends in on direction from the instrument opening 15, i.e. within the insertion tube towards the bending section tip head.

Endoscopes are fragile, complex and expensive and must consequently be treated gently during cleaning and disinfection to be usable over a long period of time. The cleaning process requires that the both the exterior of the endoscope and the interior of the endoscope control body 16, the channels through the universal cord 17 and the insertion tube 12, as well as the openings to respective channel are first cleaned carefully. After the cleaning is completed the endoscope is finally disinfected to prevent that contaminations are spread from one patient to another, or from the used endoscope to persons working with the endoscope.

Figure 2:
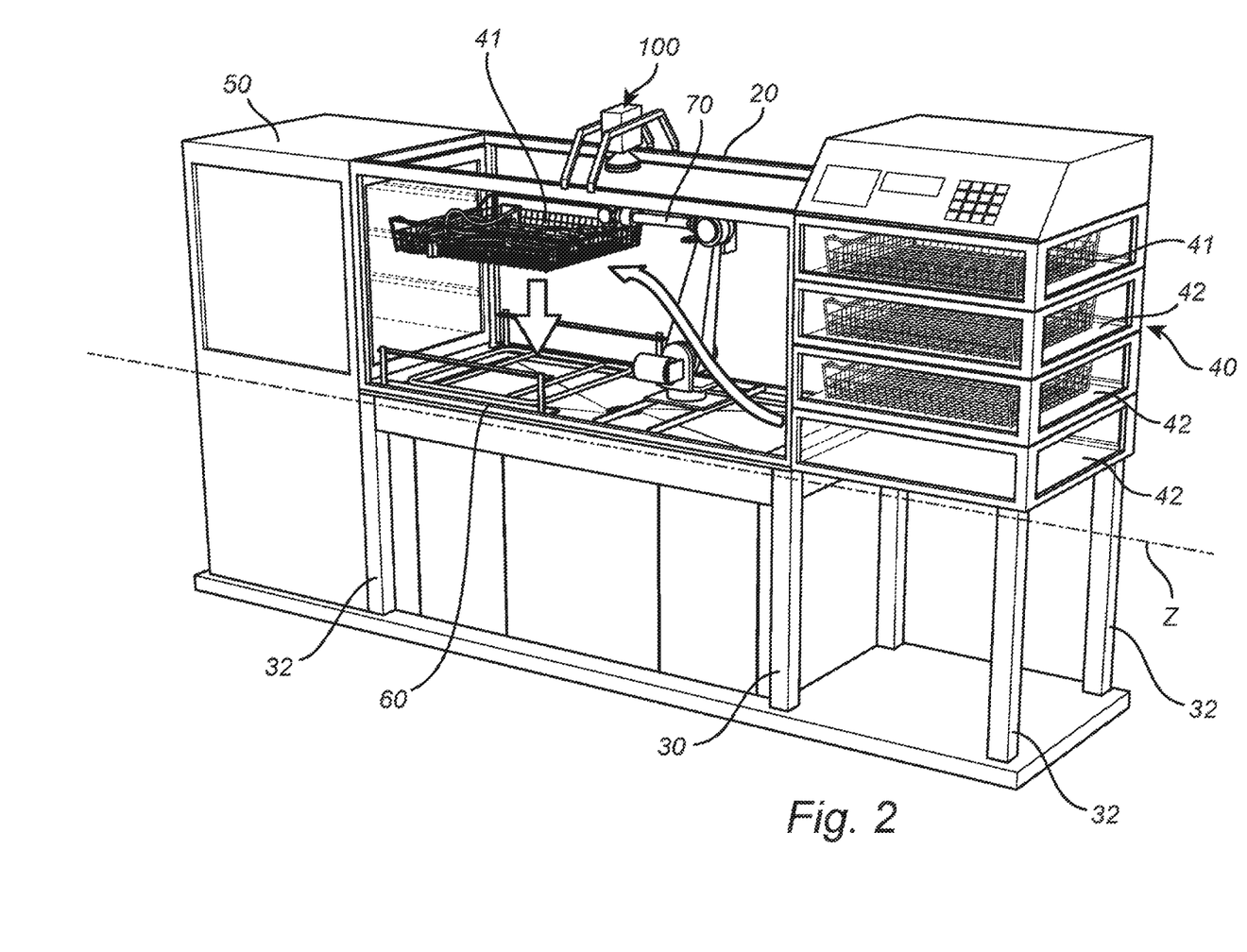
FIG. 2 illustrates a perspective view of one embodiment of the arrangement for cleaning and disinfection of endoscopes.

One embodiment of the arrangement 20 according to the invention is illustrated in perspective in FIG. 2 and the different parts of the arrangement will now be described in further detail.

The arrangement comprises a support structure 30 arranged to provide a rigid and reliable support for the different part of the arrangement arranged along a longitudinal direction Z extending in substantially horizontal direction. In the illustrated embodiment of the arrangement, the support structure comprises a number of support legs 32 extending in substantially vertical direction. The support legs are intended to be arranged on a substantially horizontal floor to support the different parts of the arrangement in a working position elevated from the floor.

In one end along the longitudinal direction, a rack 40 is arranged and in the opposite end a disinfection device 50 is arranged. Between the rack and the disinfection device a work space 60 for cleaning of endoscopes by a robotic device 70 if formed.

The rack 40 is designed to support four substantially identical trays 41 arranged on top of each other within the rack. Each rectangular tray is slidably arranged within the rack along the longitudinal direction Z and could be removed from the rack. The rack comprises guide rails extending in substantially horizontal direction within the rack parallel to the longitudinal direction so that the trays can slide along the guide rails or support shelves 42 on which the tray can rest until the cleaning is initiated. The rack is preferably accessible from a front side of the arrangement, alternatively via the side of the rack opposite to the work space, where it is easy for the operator to introduce the tray in the rack.

Figure 3:
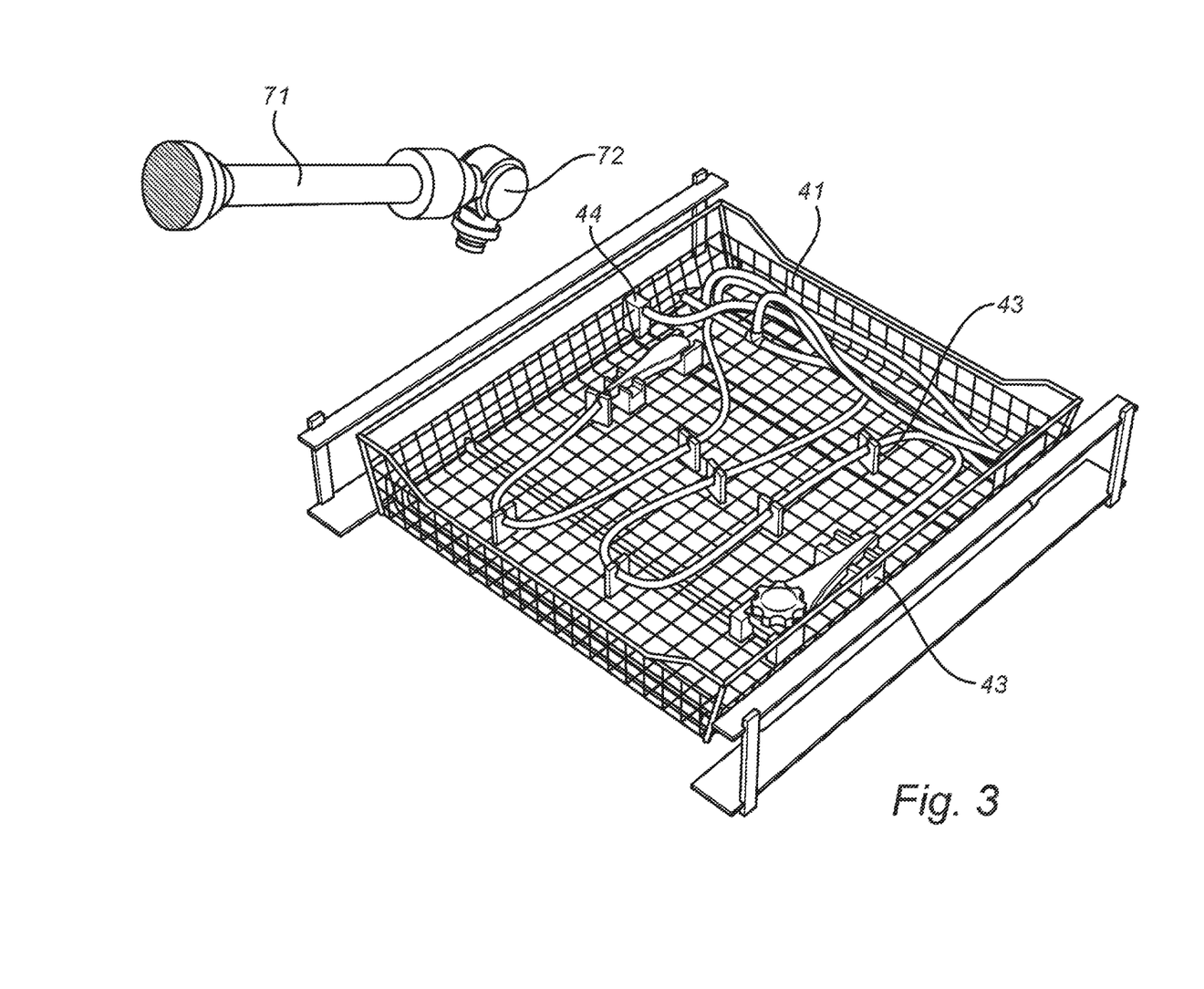
FIG. 3 illustrates a tray and one type of endoscope arranged in the tray.

The number of trays is adapted to correspond to the required capacity of the arrangement but is mostly within the range of 1 to 8. The illustrated trays are formed of a wire mesh such that cleaning and disinfection fluid is allowed to flow easily through the tray. In each tray a fixture 43 is arranged to support and maintain the endoscope in the desired position within the tray to facilitate the cleaning and ensure the desired result of the cleaning and disinfection. The tray and/or fixture furthermore comprises at least one adapter 44 that could be connected to the at least one channel in the endoscope to make it possible to a flush cleaning fluid and/or disinfection fluid through the at least one channel in the endoscope during the cleaning and/or disinfection process. Preferably the fixture and/or tray comprises several adapters 44 such that the fixture could be used for several different types of endoscopes comprising further channels. The fixture could be removably arranged within the tray such that a fixture corresponding to the type of endoscope that needs to be cleaned and disinfected is arranged within the tray by the operator when the endoscope is arranged in the tray.

Preferably each tray also comprises one or more basket for parts dismounted from the endoscope such that all components related to the endoscope are packed together within the same tray. Examples of parts dismounted from the endoscope are the channel closing adapters and the instrument adapters.

The robotic device is arranged between the rack and the disinfection device adjacent to the work space for cleaning of endoscopes. The illustrated robotic device comprises one movable robot arm 71 with a robot hand 72 arranged in the outer end of the movable robot arm. The robot hand is designed to be able to carry different gripping means and working tools.

The gripping means are designed to be able to grip the tray during movement of the tray between the rack, the work space and the disinfection device. The gripping means are furthermore intended for gripping the endoscope and parts of the endoscope that need to be dismounted to be able to conduct the desired cleaning and disinfection and dismounting of the different parts of the endoscope.

The replaceable working tool could be arranged to carry one or more brushes used during cleaning of the endoscope or any other suitable tool required to conduct the different steps of the cleaning process. The types of working tools as well as the size of the working tools used during the cleaning process are adapted to the specific type of endoscope.

The robotic device 70 is configured to dismount components from the endoscope that are necessary to remove to be able to access the interior of the endoscope control body and the at least one channel within the insert tube.

The robotic device is configured to clean the interior and exterior of the endoscope according to a predetermined program adapted to the type of endoscope that is up for cleaning by use of one or more brushes adapted to the dimensions of the endoscope and the at least one channel within the insertion tube.

The dismounting of the different parts of the endoscope as well as the cleaning of the endoscope is conducted with the endoscope arranged in the fixture within the tray, alternatively the robot is configured to move the endoscope from the tray to a working fixture, not illustrated, in which the endoscope is secured to make it possible to conduct the cleaning process in an effective way, i.e., introducing the brushes through the instrument openings 15 and the openings 19 in the endoscope control body. In order to be able to introduce the cleaning tools, i.e. the brush or brushes it is essential that the endoscope control body is reliably secured in either the fixture in the tray or the working fixture.

The illustrated embodiment of the robotic device 70 comprises one movable robot arm 71 divided into arm segments 73 but other types of robotic devices comprising further robot arms to reduce the time required for each cleaning cycle or make it possible to clean and disinfect complex types of endoscopes could also be used without departing from the general idea of the present invention. The design of the robotic device is based on well-known existing technology.

Cleaning fluid is supplied to the endoscope or the brushes by means for supplying cleaning fluid arranged either in the area of the robot hand in the end of the robotic arm, or as a separate device arranged adjacent to the robotic arm in the area of the work space.

The robotic device could be configured to be able to use different types of brushes adapted for different parts of the endoscope as well as different types of endoscopes. One advantageous type of brush is elongated with a central flexible cord to be able to extend through the channel, or channels, first within the insertion tube and then in the universal cord of the endoscope or in the opposite order. The elongated flexible cord is fed by a feeding mechanism comprising guide and feeding wheels arranged in the robot hand to move the elongated flexible cord back and forth within the channel that is cleaned.

The brush could also be combined with one or more nozzles configured to flush cleaning fluid or water during the cleaning phase, or part of the cleaning phase. The nozzles are preferably arranged to direct the spray of cleaning fluid in different directions, i.e. forwards and backwards. A further embodiment of the working tool for cleaning could rely on only using pressurized cleaning fluid distributed from the nozzles to clean the channels.

The robotic device could furthermore be configured to clean the interior and/or passages in the parts dismounted from the endoscope, i.e., the channel closing adapter and the instrument adapter. These dismounted parts are preferably also secured in either the fixture in the tray, or in the working fixture, to make it possible for the robotic device to clean the different parts. The parts are cleaned by one or more smaller brushes with a size corresponding to the size of the interior and/or the passage in that particular part.

Below the work space, a drained collecting sink 74 is arranged to collect the used cleaning fluid from the endoscope. However, in an alternative embodiment of the cleaning device the cleaning of the interior and/or exterior of the endoscope takes place by flushing a cleaning fluid on and through the endoscope under pressure to remove residuals. The arrangement furthermore comprises several different components arranged to generate the desired flow of cleaning fluid, as well as draining of used cleaning fluid from the sink below the work space but these systems are well known in the prior art and is not described in detail in this application.

The robotic device, and the different functions of the robotic device, are monitored and operated by a control unit 80 also configured to operate all the different functions and systems of the arrangement for cleaning and disinfection of endoscopes. The operator communicates and provide input and receives output from the arrangement via a user interface 90. The user interface 90 is preferably arranged on the exterior of a casing that is arranged to enclose the different parts of the arrangement to be easy for the operator to access.

Adjacent to the work space, in the opposite end of the arrangement as the rack, a disinfection device 50 is arranged. The disinfection device comprises a disinfection chamber 51 arranged to enclose one or more trays arranged within the disinfection chamber when the cleaning is completed. Once the intended number of trays are arranged within the disinfection chamber, the chamber is closed and the disinfection process initiated. The disinfection chamber preferably comprises a door arranged adjacent to the work space to prevent that residuals and/or cleaning fluid from the work space reach the already cleaned endoscopes arranged in trays in the disinfection chamber.

The disinfection device is configured to operate according to a predetermined program to distribute disinfection fluid within the disinfection chamber to disinfect the endoscope. When the disinfection device is activated, disinfection fluid is sprayed on the endoscopes by nozzles arranged within the disinfection chamber and flushed though the channel, or channels, in the endoscope via tubes connected with the adapter, or adapters, connected to the channel, or channels and arranged to flush disinfection fluid.

During the disinfection process one or more disinfection fluids optimized for different types of contamination are used to ensure the desired result.

In an alternative embodiment of the arrangement according to the invention the disinfection device is designed to disinfect one endoscope at a time and comprises a disinfection sink in which the tray, i.e. the endoscope, is arranged and the disinfection process takes place. The disinfection device furthermore comprises several different components arranged to generate the desired flow of disinfection fluid as well as draining of used disinfection fluid from the disinfection chamber but these systems are well known in the prior art and is not described in detail in this application.

The arrangement furthermore comprises an optical device 100 arranged to monitor the work space and the endoscope arranged in the tray and is in the illustrated embodiment arranged above the work space where it has a clear view over the tray arranged in the intended position within the work space. The optical device is connected to the control unit 80 and comprises means to optically identify the type of endoscope arranged in the tray as well as the position of the different parts of the endoscope within the tray. The detected information is transferred to the control unit 80 that uses the information to verify that the type of endoscope and cleaning process is correct and alert an operator if something during the operation does not proceed as intended.

The optical device could furthermore be configured to monitor the cleaning process and that the endoscope is arranged in the intended position in the tray and the at least one adapter connected to the at least one channel in the endoscope.

Figure 4:
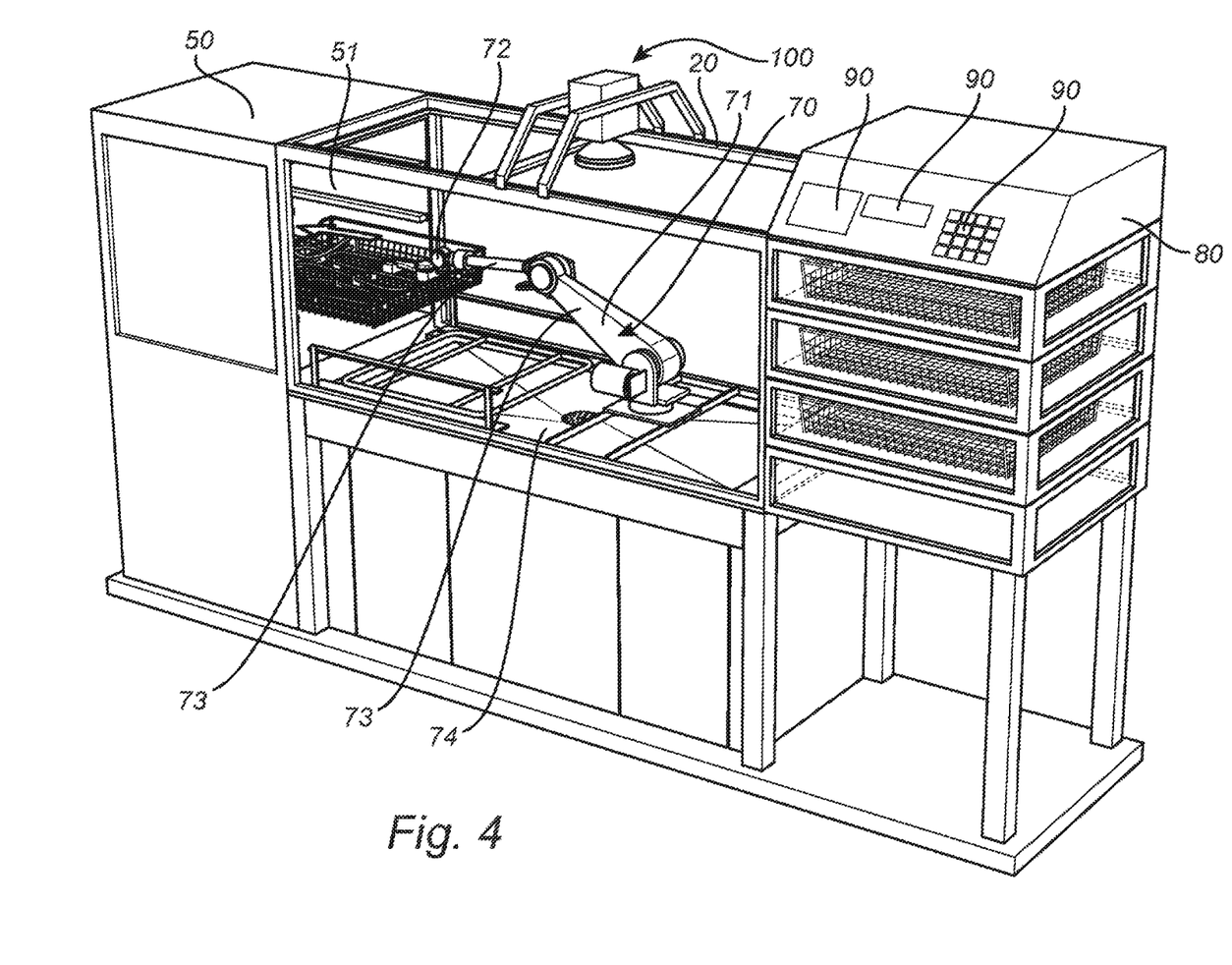
FIG. 4 illustrates the arrangement for cleaning and disinfection of endoscopes when the arrangement is configured for running the cleaning and disinfection process.
Figure 5:
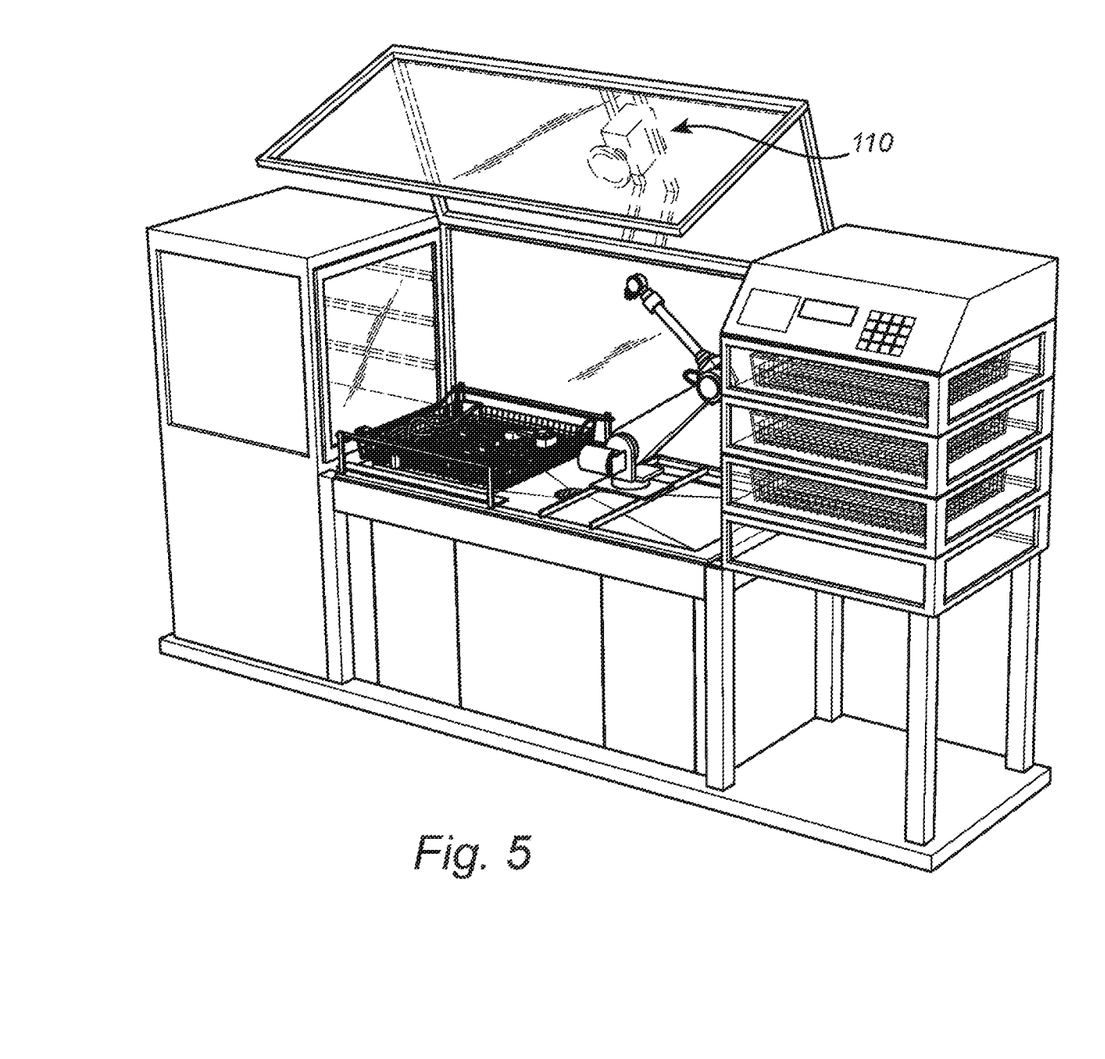
FIG. 5 illustrates the arrangement for cleaning and disinfection of endoscopes with the casing opened for inspection.

The arrangement furthermore comprises a casing 110 that is extending from the rack 40 to disinfection device 50 such that the robotic device 70 and the entire work space 60 where the dismounting and cleaning of the endoscope and dismounted components takes place is enclosed within the casing 110 thereby preventing that cleaning fluid is splashed from the work space to the area surrounding the work space. Preferably the entire rack, the work space and the disinfection device is enclosed to prevent that contaminants from the contaminated endoscopes are spread to operators working with the cleaning and disinfection and to surrounding structures or equipment.

A preferred embodiment of the arrangement furthermore comprises means to generate a pressure below that of the atmosphere surrounding the casing inside the casing to prevent that contaminants from the cleaning and disinfection is transferred from the arrangement to operators or structures in the vicinity of the arrangement. To further reduce the risk the arrangement comprises a filtration device arranged to filter air that is exiting the casing.

The present invention furthermore relates to a method for cleaning and disinfection of an endoscope using the arrangement according to the invention.

The process is initiated by the operator that first arrange the used endoscope in the intended position in the tray to make it possible for the robot hand to grip and conduct the different predetermined operations to dismount and clean the endoscope.

When the endoscope is arranged in the correct position in the tray, the tray is arranged in the rack and the type of endoscope indicated by the operator via the user interface such that the control unit can start the correct cleaning and disinfection program for this particular type of endoscope. The indication of type of endoscope is either done manually via the user interface, i.e. for example a touch-screen, or by a bar code reader connected to the control unit such that the operator is able to scan a bar code arranged on the endoscope to indicate the type of endoscope arranged in the tray.

The robotic arm moves the tray from the rack to the working space and in order to eliminate the risk that the wrong cleaning program is started due to an operator mistake during the indication of type of endoscope done by the operator, the type of endoscope in the tray is verified by the optical device before any dismounting or cleaning is initiated. In case the manual input differs from the information detected by the optical device the process is stopped and an alert, for example a sound or visible indication on the user interface, i.e. a touch-screen, is generated by the control unit such that the operator can have a second look and confirm or correct the indication of the type of endoscope in the tray.

The control unit then start the process and clean the at least one channel in the endoscope, and if desired the exterior or the endoscope according to the predetermined cleaning program. If dismounting of one or more parts is required to access the interior of the endoscope, the robot hand first dismount the part, or parts, and put them in the intended position within the tray, alternatively within one or more smaller baskets arranged in the tray to ensure that all parts are kept in order. After the cleaning is completed, the robotic device connects the at least one adapter to the at least one channel in the endoscope to prepare the endoscope for the disinfection step.

After the cleaning process is completed, the robotic arm moves the tray to the disinfector device and activate the disinfection device to start the disinfection process. In order to further reduce the risk for improper disinfection, the method may comprise an additional step conducted after the cleaning process is completed. In this additional step the optical device monitors that the endoscope is arranged in the intended position in the tray and that the at least one adapter is connected to the at least one channel in the endoscope before the disinfection is started.

One preferred embodiment of the method comprises a final cleaning up step conducted after the cleaning of the endoscope is completed. During the cleaning up step the robotic device clean the work space to remove residues from the cleaning process.

A man skilled in the art faced with the described arrangement and method would notice several possible modifications to adapt the arrangement and the method to different needs. However, the scope of protection of the claimed invention should not be limited to the embodiments described above that all could be combined in different ways without departing from the scope of protection defined by the appended claims.

The invention claimed is:

1. Arrangement for cleaning and disinfection of endoscopes comprising at least one internal channel accessible via an opening in the endoscope, said arrangement comprising:
   a support structure;
   at least one tray comprising at least one fixture arranged to maintain the endoscope in a desired position within the at least one tray;
   a rack arranged to support the at least one tray;
   a control unit arranged to control and operate the arrangement;
   a user interface connected to the control unit and configured to receive input from an operator to indicate the type of endoscope arranged in the at least one tray;
   an optical device connected to the control unit and including means to optically identify the type of endoscope arranged in the at least one tray,
   wherein the control unit is configured to receive identification information to confirm that the type of endoscope arranged in the at least one tray is the same as the indication from the operator;
   a robotic device operated by the control unit and arranged to clean the at least one channel in the endoscope;
   a disinfector device arranged to enclose the at least one tray and disinfect the endoscope; and
   a casing arranged to enclose the robotic device, wherein the rack is arranged within the casing and a closable opening is arranged in the casing to access the rack.

2. Arrangement according to claim 1, wherein the at least one fixture maintains the endoscope where it is accessible for the robotic device, and at least one adapter intended to be connected to the at least one channel in the endoscope.

3. Arrangement according to claim 2, wherein the fixture is removably arranged in the tray.

4. Arrangement according to claim 2, wherein the optical device furthermore is configured to monitor that the endoscope is arranged in the desired position in the at least one tray and that the at least one adapter is connected to the at least one channel in the endoscope.

5. Arrangement according to claim 1, wherein the the at least one fixture is removably arranged within the at least one tray, the at least one fixture comprises means for maintaining the endoscope in a secured position where it is accessible for the robotic device.

6. Arrangement according to claim 1, wherein the robotic device is configured to dismount one or more parts of the endoscope to access the at least one channel in the endoscope.

7. Arrangement according to claim 1, wherein the casing extends to the disinfector device such that the cleaning of the endoscope takes place within the casing.

8. Arrangement according to claim 1, wherein the disinfector device is arranged to flush one or more disinfection fluids on the endoscope and through the at least one channel according to a predetermined procedure to disinfect the endoscope.

9. Arrangement according to claim 1, wherein the disinfector device is arranged to involve two different disinfection fluids during the disinfection process.

10. Arrangement according to claim 1, wherein the disinfector device comprises a disinfection chamber arranged to enclose the at least one tray, and said disinfector device is configured to operate according to a predetermined program to distribute disinfection fluid within the disinfection chamber to disinfect the endoscope.

11. Arrangement according to claim 1, wherein the disinfector device is arranged within the casing and comprises a disinfection sink such that the at least one tray is arranged in the sink where the disinfection process takes place.

12. Arrangement according to claim 1, wherein the arrangement further comprises a filtration device to filter air exiting the casing.

13. Method for cleaning and disinfection of an endoscope comprising at least one internal channel accessible via an opening in the endoscope using the arrangement according to claim 1, said method comprising the steps:
   a) arrange the endoscope in the desired position in the at least one tray;
   b) indicate the type of endoscope in the at least one tray via the user interface;
   c) verifying the type of endoscope in the at least one tray with the optical device;
   d) activate the robotic device to clean the at least one channel in the endoscope;
   e) activate the disinfector device to disinfect the endoscope.

14. Method according to claim 13, wherein the the at least one fixture is removably arranged within the at least one tray, the at least one fixture comprises means for maintaining the endoscope in a secured position where it is accessible for the robotic device and said method comprises an additional step c2) conducted after step c) and before step d) in which the robotic device moves the endoscope and secures it in the at least one fixture.

15. Method according to claim 13, wherein the arrangement comprises at least one tray comprising at least one adapter intended to be connected to the at least one channel in the endoscope, and the method comprises an additional step d2) conducted after step d) and before step e) and involves connecting the at least one adapter to the at least one channel in the endoscope.

16. Method according to claim 15, wherein the method comprises an additional step conducted after step d2) where the optical device monitors that the endoscope is arranged in the intended position in the at least one tray and that the at least one adapter is connected to the at least one channel in the endoscope.

17. Method according to claim 13, wherein the robotic device initiates step d) by dismounting one or more parts of the endoscope to access the at least one channel in the endoscope.

18. Method according to claim 13, wherein the robotic device comprises means for brushing the at least one channel with an appropriate brush, and or comprises means for flushing the at least one channel in the endoscope with an appropriate cleaning fluid or an abrasive cleaning material during step d).

19. Method according to claim 13, wherein the disinfector device during step e) is arranged to conduct a number of predetermined steps to disinfect the endoscope.

20. Method according to claim 13, furthermore comprising a cleaning up step conducted after step d), wherein said robotic device during this step is configured to dean a work space within the casing to remove residues from the cleaning process.

21. Method according to claim 13, wherein the disinfector device comprises a disinfection chamber arranged to enclose the at least one tray, and said disinfection device during step e) is configured to operate according to a predetermined program to distribute a disinfection fluid within the disinfection chamber to disinfect the exterior of the endoscope and flush disinfection fluid through the at least one channel in the endoscope.

* * * * *